(12) United States Patent
Tanaka

(10) Patent No.: US 6,177,465 B1
(45) Date of Patent: Jan. 23, 2001

(54) PESTICIDAL COMPOSITION

(75) Inventor: Yasuyori Tanaka, Toyonaka (JP)

(73) Assignee: Sumitomo Chemical Company, Limited, Osaka (JP)

( * ) Notice: Under 35 U.S.C. 154(b), the term of this patent shall be extended for 0 days.

(21) Appl. No.: 09/556,407

(22) Filed: Apr. 24, 2000

(30) Foreign Application Priority Data

Apr. 28, 1999 (JP) .................................................. 11-121953

(51) Int. Cl.$^7$ .................................................. A01N 37/12
(52) U.S. Cl. .................................................. 514/535; 514/537
(58) Field of Search ....................................... 514/535, 537

(56) References Cited

FOREIGN PATENT DOCUMENTS 57-156407   9/1982 (JP) .
8-319202   12/1996 (JP) .

*Primary Examiner*—Shelley A. Dodson
*Assistant Examiner*—Alton Pryor
(74) *Attorney, Agent, or Firm*—Sughrue, Mion, Zinn, Macpeak & Seas, PLLC

(57) ABSTRACT

A pesticidal composition which comprises 2-methoxycarbonyl-4-chlorotrifluoranethanesulfonanilide as an active ingredient and at least one ester selected from the group consisting of di-$C_{2-8}$-alkyl $C_{4-10}$-alkanedicarboxylate, tri-$C_{2-4}$-alkyl citrate, tri-$C_{2-4}$-alkyl acetylcitrate and $C_{8-18}$-fatty acid ester, provides an excellent pesticidal effect.

20 Claims, No Drawings

PESTICIDAL COMPOSITION

FIELD OF THE INVENTION

The present invention relates to pesticidal compositions.

BACKGROUND ART

It is known that 2-methoxycarbonyl-4-chlorotrifluoromethanesulfonaniiide can be used as an active ingredient of an insecticidal/acaricidal coosition in Japanese Laid-open Patent Nos. sho-57-156407A and hei-8-319202A. However, its insecticidal/acaricidal effect may be insufficiently given when used as total release aerosol formulations or smoking formulations. Especially, the effect against Acaridae, particularly copra mite (*Tyrophagus putrescentiae*), that is an important object because of alergen, may be low.

SUMMARY OF THE INVENTION

The present invention provides a pesticidal composition comprising 2-methoxycarbonyl-4-chlorotrifluoromethanesulfonanilide of the formula

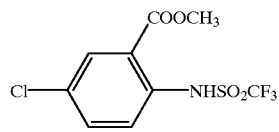

and at least one ester compound selected fron the group of specific ester compounds, which has an extremely good pesticidal activity and especially shows an excellent effect in a formulation of a total release aerosol composition, foaming composition or smoking composition.

The present pesticidal composition comprises 2-methoxycarbonyl-4-chlorotrifluoromethanesulfonanilide (hereinafter referred to as the present compound) and at least one ester compound (hereinafter referred to as the present ester) selected from the group consisting of di-$C_{2-8}$-alkyl $C_{4-10}$-alkanedicarboxylate, tri-$C_{2-4}$-alkyl citrate, tri-$C_{2-4}$-alkyl O-acetylcitrate and $C_{8-18}$-fatty acid ester.

DETAILED DESCRIPTION OF THE INVENTION

In the present invention, preferable examples of the di-$C_{2-8}$-alkyl $C_{4-10}$-alkanedicarboxylate include di-$C_{3-8}$-alkyl adipate, di-$C_{3-8}$-alkyl succinate and di-$C_{2-8}$-alkyl sebacate. Preferable examples of the $C_{8-18}$-fatty acid ester include glycerin triester of $C_{8-18}$-fatty acid and $C_{2-8}$-alkyl ester of $C_{8-18}$-fatty acid.

Typical examples of the present ester include dibutyl adipate, diisobutyl adipate, dipropyl succinate, diethyl sebacate, triethyl citrate, triethyl O-acetylcitrate, tributyl O-acetylcitrate, glyceryl tri(2-ethylhexanoate), isopropyl myristate and isopropyl isostearate.

The weight ratio of the present compound and the present ester in the present composition is usullly in the range of fran 1:1 to 1:50.

The content of the present compound in the present composition is usually 0.01 to 20% by weight, but depends on the formulation type. In aerosol formulations, foaming formulations or smoking formulations, the content of the present compound is usually 0.3 to 10% by weight. In liquid formulations such as oil formulations and emulsifiable concentrates, said content is usually 0.1 to 20% by weight. Further, in dusts, said content is usually 0.01 to 5% by weight.

In the case that the present composition is a formulation of oil formulations, emulifiable concentrates, suspensible concentrates, dusts, granules and so on, the formulation can further contain a solid carrier or an auxiliary agent such as a surfactant, dispersant, wetting agent, thickner, antioxidant, UV-absorber and organic solvent. Said solid carriers are exemplified by talc, bentonite, clay, kaolin, diatomaceous earth, silica, vermiculite and perlite. Said organic solvents are exemplified by aromatic hydrocarbons (e.g., xylene, methylnaphthalene, phenylxylylethane, alkylbenzene), ketones (e.g., acetone, methyl ethyl ketone, methyl isobutyl ketone, cyclohexanone, isophorone), alcohols (e.g., methanol, ethanol, isopropyl alcohol, hexanol, benzyl alcohol, ethylene glycol, propylene glycol, 3-methoxy-3-methyl-1-butanol), 3-methoxy-3-methyl-1-butyl acetate, N-methyl-2-pyrrolidone and propylene carbonate.

In the case that the present composition is an aerosol formulation, the present composition comprises the present compound, the present ester, a saturated hydroarbon solvent and a propellant. The content of the components is usually 0.5 to 10% by weight, 0.5 to 20% by weight, 3 to 59% by weight and 40 to 90% by weight respectively.

For controlling indoor mites, especially house dust mites, it is very effective to utilize a total release aerosol formulation. Total release aerosol is an aerosol for applying all the contents in a short period to a closed room. An actuator for total release is fitted to the aerosol container, wherein the actuator has a means for keeping a spray button pushed after the button is once pushed.

The saturated hydrocarbon solvent may be a straight-chain or branched aliphatic hydrocarbon, an alicyclic hydrocarbon or a mixture thereof. Examples of the propellant include propane, n-butane, isobutane, dimethyl ether and mixtures thereof. In these propellants, dimethyl ether is preferably utilized. Compressed gas such as nitrogen, carbon dioxide, air and so on, may be further charged for increasing the inner pressure to make the total release easy. The content of the propellant is preferably 60 to 90% by weight in the aerosol formation and the inner pressure of the aerosol container is usually 3 to 6 kg/cm$^2$ of gauge pressure at 20° C., when the aerosol is a total release aerosol.

A diameter of a sprayed mist can be varied according to a sort of aerosol valve, weight ratio of liquid/propellant, inner pressure and terminal orifice size of actuator. And it is preferable to utilize an aerosol valve for making the volume median diameter 5 to 30 $\mu$m at 30 cm from the termil orifice when the spray speed of the contents is 1 to 3 g/sec.

It is easy to apply the present cooposition to a surface or inner of carpet and mat, when the present composition is an aerosol formilation.

In the case that the present composition is a foaming formulation, the present composition cmprises the present compound, the present ester and an organic foaming agent. The content of the components is usually 0.5 to 10% by weight, 1 to 30% by weight and 60 to 97.5% by weight respectively.

Examples of the organic foaming agent include azodicarbonamide, p-toluenesulfonylhydrazide, benzenesulfonylhydrazide, azobisisobutyronitrile, 2,2'-azobisisobutyramide, 2-(carbamoylazo)isobutyronitrile, methyl-2,2'-azobisisobutyrate, 2,4-bis(azosulfonetoluene), 1,1'-azobiscyclohexanecarbonitrile and dinitrosopentamethylenetetramine. The present foaming formulation can further contain a foaming adjusting agent such as zinc oxide, magnesium oxide, calcium stearate, zinc stearate and so on.

The present foaming formulation is utilized by heating. The heating source may be a chemical reaction of calcium oxide with water or electric heater.

The present foaming formulation can be granules, which are usually prepared by kneading the present compound, the present ester, an organic foaming agent and so on with water, extruded, dried and molded to 1 to 5 mm granules. For making the molding easy, it is preferable to add a binder to the formulation. Said binder may be methylcellulose, hydroxymethylcellulose, hydroxypropylceliulose, water soluble starch and so on. The present foaming formulation can also be prepared by making granules without the present compound or the present ester and then adding the present compound and the present ester or their solution dissolved with a volatile solvent such as acetone, dichloromethane and so on, if necessary.

The present foaming formulations are usually charged in a container such as a metal container and utilized by heating the container fran outside by the above-mentioned heating source.

In the case that the present composition is a smoking formulation, the present composition comprises the present compound, the present ester, nitrocellulose, an organic foaming agent and an oxidizing agent. The content of the components is usually 0.3 to 10% by weight, 0.3 to 20% by weight, 2 to 20% by weight, 5 to 30% by weight, and 5 to 30% by weight respectively.

In the present smoking formulation, nitrocellulose may be used as a solid solution mixed with a plasticizer such as dibutyl phthalate and tricresyl phosphate or as celluloid.

Examples of the oxidizing agent include perchlorate salts such as ammonium perchlorate, potassium perchlorate and sodium perchlorate, and chlorate salts such as potassium chlorate.

The present smoking formulation can further contain a foaming adjusting agent mentioned above, a degradation accelerator for oxidizing agent, an exothermic adjusting agent an so on. Examples of the degradation accelerator for oxidizing agent include iron chloride, copper chloride, potassium chloride, sodium chloride, iron oxide, copper oxide, chromium oxide, bis(cyclopentadienyl)iron and examples of the exothenmic adjusting agent include nitrate such as potassium nitrate, ammonium nitrate and guanidine nitrate, guanylurea phosphate and guanidine sulfamate. Moreover, the present smoking formulation may preferably contain a combustible substance such as sugars (e.g., lactose), ceflulose and wood powder, and a binder mentioned above.

The present smoking formulation can be granules, which are usually prepared by kneading the present compound, the present ester, nitrocellulose, an organic foaming agent and an oxidizing agent, and optionally a foaming adjusting agent, a degradation accelerator for oxidizing agent, an exothermic adjusting agent, a combustible substance and so on with water, extruded, dried and molded to 1 to 5 mm granules. The present smoking formulation can be set in a cylidrical container, for example made of paper, and fitted with an igniter such as a molded thermit.

The present smoking formulation may be a mixture of granules comprising the present compound, the present ester, nitrocellulose and an organic foaming agent with granules comprising the oxidizing agent and combustible substance. Further, the present smoking formulation may be a pile consisting of an upper layer comprising the present compound, the present ester, nitrocellulose and an organic foaming agent and a lower layer comprising the oxidizing agent, and it can be set in a cylidrical container and the lower layer can be fitted with an igniter such as a molded thermit.

The present composition can comprises the other pesticidal compound.

The other pesticidal compounds are illustrated by pyrethroid coppounds and carbamate compounds. Phenothrin, permethrin, cyphenothrin and their pesticidally active isomers are preferable as the pyrethroid coopound, and metoxadiazon and propoxur are preferable as the carbamate compounds. Further, phenyl salicylate, benzyl benzoate and diethyl terephthalate are also illustrated as the other pesticidal compounds. In those cases, the mixing ratio of the present compound and the other pesticidal compound is usually in the rage of from 1:0.5 to 1:5 by weight.

Example of the pests controlled by the present composition include acarina and insects. They are exemplified by indoor mites (for example, *Dermatophagoides spp.* such as *Dermatophagoides farinae, Dermatophagoides pteronyssinus* and so on; Acaridae such as *Lardoglyphus konoi, Tyrophagus putrescentiae, Aleuroglyphus ovatus* and so on; Glycyphagidae such as *Glycyphagus privatus, Glycyphagus domesticus, Glycyphagus destructor* and so on; Cheyletidae such as *Chelacaropsis moorei, Chelacaropsis malaccensis, Cheyletus fortis, Cheyletus eruditus, Chelatomorpha lepidopterorum* and so on; Macronyssidae such as *Ornithonyssus bacoti, Ornithonyssus sylviarum, Dermanyssus gallinae, Dermanyssus hirundinis* and so on; *Haplochthonius spp.*; Pyemotidae; itch mites; and so on); fleas such as cat flea, dog flea and so on; cockroaches such as German cockroach, American cockroach, smokeybrown cockroach and so on; Psocoptera such as *Liposcelis bostrychophilus, Liposcelis entomophilus* and so on; Formicidae such as *Monomorium pharaonis* and so on; Cimicidae such as *Cimex lectularius* and so on. Especially, the present composition is very effective for controlling indoor mites.

The present copposition is utilized by applying pests, especially mites directly or a locus where the pests inhabit. The application dosage is usually 5 to 100 mg per 1 m$^2$. When the present composition is a formulation for applying in a closed room such as foaming formulation, smoking formulation and total release aerosol, the application dosage is usually 5 to 50 mg per 1 m$^3$ of a closed room.

EXAMPLES

The present invention will be explained in detail by examples below, but the present invention is not limited to these examples.

Preparation Example 1

A solution, which was obtained by dissolving 82 mg of 2-methoxycarbonyl-4-chlorotrifluorooethanesufonanilide in 2.5 g of diisobutyl adipate, was charged in a 50 ml-volume aerosol container. Hydrocarbon solvent (Isoper E, manufactured by Exxon Chemical) was added thereto to make the total 6.25 g. After an aerosol valve was crimped to the aerosol container, 18.75 g of dimethyl ether was charged, and then an actuator for total release aerosol was fitted to give the present aerosol formulation 1.

Reference Preparation Example 1

In a 50 ml-volume aerosol container, 82 mg of 2-methoxycarbonyl-4-chlorotrifluormetnanesufonanilide was charged and petroleum solvent (Isoper E, manufactured by Exxon Chemical) was added thereto to make the total 6.25 g. After an aerosol valve was crimped to the aerosol container, 18.75 g of dimethyl ether was charged, and then an actuator for total release aerosol was fitted to give the reference aerosol formulation 1.

Test example 1

Filter paper having 4 cm in diameter was put on an aluminum plate and the filter paper was surrounded by adhesives for preventing from running away of mites. And then, about ten to twenty house dust mites (*Tyrophagus putrescentiae*) were released on the filter paper.

At three corners of the bottom of a 1.8 m cubed chamber, three aluminum plates above were put at intervals of 30 cm fron the corners. On the other hand, the present aerosol formulation or the reference aerosol formulation was put on the botton at the center in the tightly closed chamber, and by pressing the actuator the contents were totally released. After two hours, the aluminum plates were taken out and the mortality of the mites was counted after 3 days. The ratio of the number of the dead mites against the number of all the mites on the filter paper was calculated for the mortality. The results are shown in Table 1.

TABLE 1

| Tested Aerosol Formulation | Mortality of mites (%) |
| --- | --- |
| Present Aerosol Formulation 1 | 100 |
| Reference Aerosol Formulation 1 | 20 |

Preparation Example 2

A solution, which was obtained by mixing 0.56 g of 2-methoxycarbonyl-4-chlorotrifluoranethanesufonanilide with 2.24 g of diisobutyl adipate, was impregnated in 8.25 g of 1 to 5 mm granules, consisting of 2.43 g of azodicarbonamide; 1.46 g of nitrocellulose, 0.52 g of zinc oxide; 0.10 g of polyvinyl alcohol; and perlite, and dried to give granules. Further, 0.56 g of d-phenothrin and 0.90 g of metoxadiazon were dissolved in a small amount of methylene chloride, dropped and impregnated in the granules given above and dried at roon temperature to give pesticidal granules. Fifteen grams (15.0 g) of 1 to 4 mm granular composition, obtained fran 1.80 g of potassium perchlorate; 0.75 g of potassium nitrate; 0.45 g of guanidine nitrate; 1.41 g of lactose; 2.70 g of alumina; 3.60 g of iron oxide; binder; and kaolin, were charged in a paper cylindrical container having 3.4 cm in inner diameter and 8 cm in height fitted with an igniter. Then, the pestidal granules were charged thereon and the container was covered with a mesh to give the present smoking formulation 1.

Preparation Example 3

The same procedures as Preparation Example 2, except that 2.24 g of tributyl O-acetylcitrate was used in place of 2.24 g of diisobutyl adipate to give the present smoking formulation 2.

Preparation Example 4

The same procedures as Preparation Example 2, except that 2.24 g of triethyl citrate was used in place of 2.24 g of diisobutyl adipate to give the present smoking formulation 3.

Preparation Example 5

The same procedures as Preparation Example 2, except that 2.24 g of triethyl O-acetylcitrate was used in place of 2.24 g of diisobutyl adipate to give the present smoking formulation 4.

Preparation Example 6

The same procedures as Preparation Example 2, except that 5.04 g of isopropyl isostearate was used in place of 2.24 g of diisobutyl adipate to give the present smoking formulation 5.

Reference Preparation Example 2

In a small amount of methylene chloride, 0.56 g of 2-methoxycarbonyl-4-chlorotrifluoromethanesufonanilide, 0.56 g of d-phenothrin and 0.90 g of metoxadiazon were dissolved, dropped, impregnated in 8.25 g of 1 to 5 mm granules, consisting of 2.43 g of azodicarbonamide; 1.46 g of nitrocellulose; 0.52 g of zinc oxide; 0.10 g of polyvinyl alcohol; and perlite, and dried at room temperature to give pesticidal granules. Fifteen grams (15.0 g) of 1 to 4 mm granular composition, obtained from 1.80 g of potassium perchlorate; 0.75 g of potassium nitrate; 0.45 g of guanidine nitrate; 1.41 g of lactose; 2.70 g of alumina; 3.60 g of iron oxide; binder; and kaolin, were charged in a paper cylindrical container having 3.4 cm in inner diameter and 8 cm in height fitted with an igniter. Then, the pesticidal granules were charged thereon and the container was covered with a mesh to give a reference smoking formulation 1.

Test example 2

At three corners of the bottom of a chamber (28 m$^3$, 3 m×4 m at bottom), three sheets of filter paper having 6 cm×12 cm in size were put at intervals of 50 cm fran the corners. In the center of the chamber, each of the smoking formulations obtained in Preparation Examples 2 to 6 and Reference Preparation Examples 2 was set on the bottom at the canter and ignited. After 2 hours, the filter paper was taken, folded in two, both sides were pasted in 5 mm width and clipped to make a bag of 6 cm×6cm. After binding both sides, about twenty to fifty house dust mites (*Tyrophagus putrescentiae*) and a small amount of food were put in the bag and clipped on the open part. The bag was kept at 25° C. and 65 to 75% of humidity for 3 days, and then, the number of dead or moribund mites was counted. The ratio of the sum of the dead and moribund mites to all the tested mites was calculated for controlling ratio. The results are shown in Table 2.

TABLE 2

| Tested Smoking Formulation | Controlling Ratio (%) |
| --- | --- |
| Present Smoking Formulation 1 | 92 |
| Present Smoking Formulation 2 | 85 |
| Present Smoking Formulation 3 | 95 |
| Present Smoking Formulation 4 | 97 |
| Present Smoking Formulation 5 | 97 |
| Reference Smoking Formulation 1 | 50 |

The same test was perforrmd, except that American house dust mite (*Dermatophagoides farinae*) was used in place of *Tyrophagus putrescentiae*, to give 100% of the controlling ratios for the present smoking formulations 1 to 5 respectively.

Preparation Example 7

A solution, which was obtained by mixing 0.116 g of 2-methoxycarbonyl-4-chlorotrifluorcmethanesufonanilide with 0.464 g of glyceryl tri(2-ethylhexanoate), was impregnated in 5.0 g of 1 to 5 mm granules, consisting of 1.47 g of azodicarbonamide; 0.88 g of nitrocellulose; 0.32 g of zinc oxide; 0.06 g of polyvinyl alcohol; and perlite, and dried to give granules. Further, 0.116 g of d-phenothrin and 0.186 g of metoxadiazon were dissolved in a small amount of methylene chloride, dropped and impregnated in the granules given above and dried at roan temperature to give pesticidal granules. Seven and a half grams (7.5 g) of 1 to 4 mm granular combustible composition, obtained frm 0.90 g of potassium perchlorate; 0.38 g of potassium nitrate; 0.23 g of guanidine nitrate; 0.71 g of lactose; 1.35 g of alumina; 1.80 g of iron oxide; binder; and kaolin, were charged in a paper cylindrical container having 3.4 cm in inner diameter and 4 cm in height fitted with an igniter. Then, the pestidal granules were charged thereon and the container was covered with a mesh to give the present smoking formulation 6.

Preparation Example 8

The same procedures as Preparation Example 7, except that 0.464 g of tributyl O-acetylcitrate was used in place of 0.464 g of gryceryl tri(2-ethylhexanoate) to give the present smoking formulation 7.

Test Example 4

Plastic cups having 3 male and 3 female smokybrown cockroaches (*Periplaneta fuliginosa*) insides were put on the two opposite corners of the bottom in a 1.8 m cubed chamber. Then, each of the smoking formulations obtained in Preparation Examples 6 and 7 were set in the center of the room and ignited. After 120 minutes, the tested insects were transferred to another cup, and the mortality after 3 days was observed. The results are shown in Table 3.

TABLE 3

| Tested Smoking Formulation | Mortality (%) |
|---|---|
| Present Smoking Formulation 6 | 100 |
| Present Smoking Formulation 7 | 92 |

Preparation Example 9

A solution, obtained by dissolving 0.50 g of 2-methoxycarbonyl-4-chlorotrifluoromethanesufonanilide in 2.00 g of triethyl citrate with heating, and 0.80 g of metoxadiazon and 0.50 g of d-phenothrin were charged in a 100 ml-volume aerosol container, and made the total 10.00 g by adding Isoper G (aliphatic hydrocarbon solvent manufactured by Exxon Chemical). After an aerosol valve was crimped to the aerosol container, 40.00 g of dimethyl ether was charged, and then an actuator for total release aerosol was fitted to give the present aerosol formulation 2.

Test example 5

At three corners of the bottom of a chamber (28 m³, 3 m×4 m at bottom), three sheets of filter paper having 6 cm×12 cm in size were put at intervals of 50 cm from the corners. In the center of the tightly closed chamber, the present aerosol formulation 2 was set on the bottom at the center and the contents were totally released by pressing the actuator. After 2 hours, the filter paper was taken, folded in two, both sides were pasted in 5 mm width and clipped to make a bag of 6 cm×6 cm. After binding both sides, about ten mites (*Chelacaropsis moorei*) were put in the bag and clipped on the open part. The bag was kept at 25° C. and 65 to 75% of humidity for 3 days, and then, the number of dead or moribund mites was counted. The ratio of the sum of the dead and moribund mites to all the tested mites was calculated for controlling ratio. AS the result, the percent moribund was 88%.

Preparation Example 10

A solution, obtained by dissolving 0.116 g of 2-methoxycarbonyl-4-chlorotrifluoromethanesufonanilide in 0.464 g of tributyl O-acetylcitrate with heating, and 0.046 g of metoxadiazon and 0.302 g of d-phenothrin were dissolved in a small amount of methylene chloride. On the other hand, 0.5 part by weight of zinc oxide, 2.2 parts by weight of water soluble starch and 97.3 parts by weight of azodicarbonamide were kneaded with an appropriate amount of water, extruded and dried to give 1 to 5 mm granules. To 5.00 g of the granules, the methylene chloride solution obtained above was dropped and dried to give the present foaming formulation 1. The present foaming formulation 1 was charged in a metal container having a heater by a chemical reaction of calcium oxide with water and utilized for test example 6.

Reference Preparation Example 3

In a small amount of methylene chloride, 0.116 g of 2-methoxycarbonyl-4-chlorotrifluoromethanesufonanilide, 0.046 g of metoxadiazon and 0.302 g of d-phenothrin were dissolved. On the other hand, 0.5 part by weight of zinc oxide, 2.2 parts by weight of water soluble starch and 97.3 parts by weight of azodicarbonamide were kneaded with an appropriate amount of water, extruded and dried to give 1 to 5 mm granules. To 5.00 g of the granules, the methylene chloride solution obtained above was dropped and dried to give a reference foaming formulation 1. The reference foaming formulation 1 was charged in a metal container having a heater by a chemical reaction of calcium oxide with water and utilized for test example 6.

Test Example 6

Filter paper having 3.8 cm in diameterwas put on an aluminum plate and the filter paper was surrounded by adhesives for preventing from runing away of house dust mites. And then, about thirty mites (*Tyrophagus putrescentiae*) were released on the filter paper.

At three corners of the bottom of a 1.8 m cubed chamber, three aluminum plates above were put at intervals of 30 cm from the corners. On the other hand, present foaming formulation 1 and the reference foaming formulation 1 in a metal container respectively were set on the bottom at the center in the chamber and heated by the chemical reaction of calcium oxide with water. After two hours the aluminum plates were taken out, and the mortality of the house dust mites were counted after one day. The ratio of the number of the dead mites against the number of all the mites on the filter paper was calculated for the mortality. The results are shown in Table 4.

TABLE 4

| Tested Foaming Formulation | Mortality (%) |
|---|---|
| Present Foaming Formulation 1 | 83 |
| Present Foaming Formulation 1 | 50 |

Preparation Example 11

A solution, which is obtained by mixing 0.50 g of 2-methoxycarbonyl-4-chlorotrifluoranathanesufonanilide with 2.00 g of tributyl O-acetylcitrate, is impregnated in 8.25 g of 1 to 5 mm granules, consisting of 2.43 g of azodicarbonamide; 1.46 g of nitrocellulose, 0.52 g of zinc oxide; 0.10 g of polyvinyl alcohol; and perlite, and dried at room temperature to give granules. Further, 0.50 g of d-phenothrin and 1.00 g of metoxadiazon are dissolved in a small amount of methylene chloride, dropped and imregnated in the granules given above and dried at room temperature to give pesticidal granules. Fifteen grams (15.0 g) of 1 to 4 mm granular composition, obtained from 1.80 g of potassium perchlorate; 0.75 g of potassium nitrate; 0.45 g of guanidine nitrate; 1.41 g of lactose; 2.70 g of alumina; 3.60 g of iron oxide; binder; and kaolin, are charged in a paper cylindrical container having 3.5 cm in diameter and 8 cm in height fitted with an igniter. Then, the pestidal granules are charged thereon and the container is covered with a mesh to give the present smoking formulation 8.

Preparation Example 12

A half (0.5) part by weight of zinc oxide, 2 parts by weight of α-starch and 61.5 parts by weight of azodicarbonamide are kneaded with an appropriate amount of water, extruded and dried to give 1 to 5 mm granules. A solution, obtained by dissolving 8 parts by weight of 2-methoxycarbonyl-4-chlorotrifluoromethanesufonanilide; 16 parts by weight of tributyl O-acetylcitrate; 2 parts by weight of metoxadiazon; and 10 parts by weight of d-phenothrin in a small amount of methylene chloride, is impregnated in the granules above and dried to give the present foaming fornmlation 2. The present foaming formulation 2 is charged in a metal container having a heater by a chemical reaction of calcium oxide with water and utilized.

Preparation Example 13

A half (0.5) part by weight of zinc oxide, 2 parts by weight of α-starch and 68.5 parts by weight of azodicarbonamide are kneaded with an appropriate amount of water, extruded and dried to give 1 to 5 mm granules. A solution, obtained by dissolving 5 parts by weight of 2-methoxycarbonyl-4-chlorotrifluorcmthanesufonanilide; 10 parts by weight of tributyl O-acetylcitrate; 4 parts by weight of metoxadiazon; and 10 parts by weight of d-phenothrin in a small amount of methylene chloride, is impregnated in the granules above and dried to give the present foaming formulation 3. The present foaming formulation 2 is charged in a metal container having a heater by a chemical reaction of calcium oxide with water and utilized.

Preparation Example 14

A solution, which is obtained by dissolving 0.5 part by weight of 2-methoxycarbonyl-4-chlorotrifluoromethanesufonanilide and 0.5 part of permethrin in 5 parts by weight of triethyl citrate with heating, is charged in an aerosol container. Hydrocarbon solvent (Isoper G. manufactured by Exxon Chemical) is added thereto to make the total 20 parts by weight. After an aerosol valve was crimped to the aerosol container, 80 parts by weight of dimethyl ether is charged, and then an actuator for total release aerosol is fitted to give the present aerosol formulation 3.

Preparation Example 15

The same procedure as Preparation Exanple 14 is performed, except that 0.3 part by weight of (S)-α-cyano-3-phenoxybenzyl (1R)-cis, trans-chrysanthemate is used in place of 0.5 part by weight of penrethrin, to give the present aerosol formulation 4.

Preparation Example 16

A solution, which is obtained by dissolving 0.5 part by weight of 2-methoxycarbonyl-4-chlorotrifluoranethanesufonanilide in 2.5 parts by weight of benzyl benzoate and 5 parts by weight of triethyl citrate, is charged in an aerosol container. Hydrocarbon solvent (Isoper E, manufactured by Exxon Chemical) is added thereto to make the total 60 parts by weight. After an aerosol valve is crieped to the aerosol container, 40 parts by weight of dimethyl ether is charged, and then an actuator is fitted to give the present aerosol formulation 16.

What is claimed is:

1. A pesticidea composition which comprises 2-methoxycarbonyl-4-chlorotrifluoromethanesulfonanilide as an active ingredient and at least one ester selected frm the group consisting of di-$C_{2-8}$-alkyl $C_{4-10}$-alkanedicarboxylate, tri-$C_{2-4}$-alkyl citrate, tri-$C_{2-4}$-alkyl O-acetylcitrate and $C_{8-18}$-fatty acid ester.

2. A pesticidal composition according to claim 1, wherein the ester is a di-$C_{2-8}$-alkyl $C_{4-10}$-alkanedicarboxylate.

3. A pesticidal composition according to claim 2, wherein the ester is a di-$C_{3-8}$-alkyl adipate.

4. A pesticidal composition according to claim 2, wherein the ester is a di-$C_{3-8}$-alkyl succinate.

5. A pesticidal composition according to claim 2, wherein the ester is a di-$C_{2-8}$-allyl sebacate.

6. A pesticidal coosition according to claim 1, wherein the ester is a tri-$C_{2-4}$-alkyl citrate.

7. A pesticide compsition according to claim 1, wherein the ester is a tri-$C_{2-4}$-alkyl O-acetylcitrate.

8. A pesticidal composition according to claim 1, wherein the ester is a $C_{8-18}$-fatty acid ester.

9. A pesticidal composition according to claim 8, wherein the $C_{8-18}$-fatty acid ester is a glycerin triester of $C_{8-18}$-fatty acid.

10. A pesticidal composition according to claim 8, wherein the $C_{8-18}$-fatty acid ester is a $C_{2-18}$-alkyl ester of $C_{8-18}$-fatty acid.

11. A pesticidal composition according to claim 1, wherein the ester is dibutyl adipate, dilsobutyl adipate, dipropyl succinate, diethyl sebacate, triethyl citrate, triethyl O-acetylcitrate, tributyl O-acetylcitrate, glyceryl tri(2-ethylhexanoate), isopropyl myristate or isopropyl isostearate.

12. A pesticidal composition according to claim 1, wherein the weight ratio of 2-methoxycarbonyl-4-chlorotrifluoromethanesulfonanilide and the ester in the pesticidal composition is in the range of 1:1 to 1:50.

13. A pesticidal composition according to claim 1, which further contains a saturated hydrocarbon solvent and a propellant.

14. A pesticidal coposition according to claim 13, wherein the contents of 2-methoxycarbonyl-4-chlorotrifluoramthanesulfonanilide, the ester, the saturated hydrocarbon solvent and the propellant are 0.5 to 10% by weight, 0.5 to 20% by weight, 3 to 59% by weight and 40 to 90% by weight respectively.

15. A pesticidal composition according to claim 1, which further contains an organic foaming agent.

16. A pesticidal composition according to claim 15, wherein the contents of 2-methoxycarbonyl-4-chlorotrifluoremethanesulfonanilide, the ester and the organic foaming agent are 0.5 to 10% by weight, 1 to 30% by weight and 60 to 97.5% by weight respectively.

17. A pesticidea coosition according to claim 1, which further contains nitrocellulose, an organic foaming agent and an oxidizing agent.

18. A pesticidal composition according to claim 17, wherein the contents of 2-methoxycarbonyl-4-chlorotrifluoramethanesulfonanilide, the ester, nitrocellulose, an organic foaming agent and an oxidizing agent are 0.3 to 10% by weight, 0.3 to 20% by weight, 2 to 20% by weight, 5 to 30% by weight, and 5 to 30% by weight respectively.

19. A method for controlling pests which comprises applying the pesticidal composition described in claim 1 to pests or a locus where pests inhabit.

20. A method according to claim 19, wherein the pests are indoor mites.

* * * * *